(12) United States Patent
Yu et al.

(10) Patent No.: US 10,315,981 B2
(45) Date of Patent: Jun. 11, 2019

(54) PROCESS FOR PREPARING A DIARYL CARBONATE

(71) Applicant: SHELL OIL COMPANY, Houston, TX (US)

(72) Inventors: Kunquan Yu, Katy, TX (US); Garo Garbis Vaporciyan, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/778,944

(22) PCT Filed: Nov. 24, 2016

(86) PCT No.: PCT/EP2016/078632
§ 371 (c)(1),
(2) Date: May 24, 2018

(87) PCT Pub. No.: WO2017/089441
PCT Pub. Date: Jun. 1, 2017

(65) Prior Publication Data
US 2018/0354887 A1 Dec. 13, 2018

(30) Foreign Application Priority Data
Nov. 26, 2015 (EP) .................... 15196610

(51) Int. Cl.
*C07C 68/06* (2006.01)
*C07C 68/08* (2006.01)
*C07C 69/96* (2006.01)

(52) U.S. Cl.
CPC ............. *C07C 68/065* (2013.01); *C07C 68/08* (2013.01); *C07C 69/96* (2013.01); *C07C 2521/06* (2013.01); *Y02P 20/127* (2015.11)

(58) Field of Classification Search
CPC .................................................. C07C 68/065
See application file for complete search history.

(56) References Cited

U.S. PATENT DOCUMENTS

| | | | |
|---|---|---|---|
| 5,334,742 A | 8/1994 | Schon et al. | |
| 5,344,954 A | 9/1994 | Schon et al. | |
| 5,747,609 A | 5/1998 | Komiya et al. | |
| 6,294,684 B1 | 9/2001 | de Bruin et al. | |
| 8,110,698 B2 * | 2/2012 | Ryu | B01J 37/0203 558/275 |
| 8,530,606 B2 | 9/2013 | Nisbet et al. | |
| 8,569,534 B2 * | 10/2013 | Ryu | B01J 37/0203 558/275 |
| 2015/0136238 A1 | 5/2015 | Trovant et al. | |

FOREIGN PATENT DOCUMENTS

| | | |
|---|---|---|
| CN | 102702500 A | 10/2012 |
| EP | 1956036 A1 | 8/2008 |
| EP | 2036880 A2 | 3/2009 |
| EP | 2135857 A2 | 12/2009 |
| EP | 2540697 A1 | 1/2013 |
| JP | 6157424 A | 6/1994 |
| WO | 2005026235 A1 | 3/2005 |
| WO | 2008090107 A1 | 7/2008 |
| WO | 2009010486 A1 | 1/2009 |
| WO | 2011014374 A2 | 2/2011 |

OTHER PUBLICATIONS

International Search Report and Written Opinion received for PCT Patent Application No. PCT/EP2016/078632, dated Jan. 23, 2017, 9 pages.

* cited by examiner

*Primary Examiner* — Golam M Shameem
(74) *Attorney, Agent, or Firm* — James D. Carruth

(57) ABSTRACT

A process for preparing a diaryl carbonate from a dialkyl carbonate and an aryl alcohol is disclosed. The process takes place in apparatus comprising at least two distillation columns, and at least one of the distillation columns is operated at subatmospheric pressure which is achieved using vacuum equipment.

8 Claims, No Drawings

PROCESS FOR PREPARING A DIARYL CARBONATE

CROSS REFERENCE TO RELATED APPLICATIONS

This is a national stage application of International application No. PCT/EP2016/078632, filed 24 Nov. 2016, which claims benefit of priority of European application No. 15196610.8, filed 26 Nov. 2015.

FIELD OF THE INVENTION

The present invention relates to a process for preparing a diaryl carbonate from a dialkyl carbonate and an aryl alcohol.

BACKGROUND OF THE INVENTION

Diaryl carbonates such as diphenyl carbonate may be prepared by a process wherein a dialkyl carbonate such as diethyl carbonate or dimethyl carbonate is reacted with an aryl alcohol such as phenol. The process is often carried out in two steps: a first step wherein the diaryl carbonate is reacted with the aryl alcohol in the presence of a transesterification catalyst to provide an alkyl aryl carbonate, and a second step wherein the alkyl aryl carbonate undergoes disproportionation to provide a diaryl carbonate and a dialkyl carbonate. Examples of such processes are disclosed in U.S. Pat. No. 5,344,954, WO2011014374 and WO2011067263.

The process is typically carried out in a series of distillation columns, some of which are operated at subatmospheric pressure. The present inventors have observed that air can leak into the distillation columns operated at subatmospheric pressure with a number of negative consequences. Oxygen and moisture from the air can cause side reactions to form undesirable trace impurities and colour bodies. They can also react with the catalyst, causing it to deactivate and, with homogeneous catalysts, precipitate out of the reaction solution. The present inventors have sought to provide a process which avoids these problems.

SUMMARY OF THE INVENTION

Accordingly, the present invention provides
a process for preparing a diaryl carbonate from a dialkyl carbonate and an aryl alcohol comprising:
a first step wherein the dialkyl carbonate reacts with the aryl alcohol in the presence of a transesterification catalyst to provide alkyl aryl carbonate and alkyl alcohol; and
a second step wherein the alkyl aryl carbonate undergoes disproportionation to yield diaryl carbonate and dialkyl carbonate;
wherein the process takes place in apparatus comprising at least two distillation columns, and at least one of the distillation columns is operated at subatmospheric pressure which is achieved using vacuum equipment;
and wherein the at least one distillation column that is operated at subatmospheric pressure has undergone a leak test and the leak test shows an air leakage rate of no greater than $2 \times 10^{-3}$ mbar·L/s.

The present inventors have found that by ensuring that there is very limited oxygen ingress into the distillation column operated at subatmospheric pressure, it is possible to reduce the problems of side reactions and catalyst deactivation. Reducing the amount of side reactions should improve the product quality and reduce the need for bleed out of heavy components. Reducing catalyst deactivation should reduce the need to replenish the catalyst. By following standard procedures for design and implementation of chemical processes, the skilled person would not have adequately minimised the oxygen ingress and would have suffered problems of product quality and catalyst deactivation. The present inventors have recognised that the process for preparing a diaryl carbonate can be improved by adopting extra measures to reduce oxygen ingress.

DETAILED DESCRIPTION OF THE INVENTION

The invention provides a process for preparing diaryl carbonate from a dialkyl carbonate and an aryl alcohol. The alkyl group in the dialkyl carbonate and alkyl aryl carbonate suitably has 1 to 4, preferably 1 to 3 carbon atoms. Preferably the alkyl group is a methyl group or ethyl group, more preferably an ethyl group. Therefore preferably the dialkyl carbonate is dimethyl carbonate or diethyl carbonate, more preferably diethyl carbonate. The aryl group in the aryl alcohol, alkyl aryl carbonate and diaryl carbonate suitably has 6 to 12 carbon atoms. Preferably the aryl group is a phenyl group. Therefore preferably the aryl alcohol is phenol and the diaryl carbonate is diphenyl carbonate. Suitable examples of the alkyl aryl carbonate are methyl phenyl carbonate and ethyl phenyl carbonate.

In the first step the dialkyl carbonate reacts with the aryl alcohol in the presence of a transesterification catalyst to provide alkyl aryl carbonate and alkyl alcohol. The transesterification catalyst may be homogeneous or heterogeneous. Possible catalysts include oxides, hydroxides, alcoholates, amides and hydrides of alkali and alkaline earth metals, e.g. sodium or potassium hydroxide, or sodium or potassium methanolate or ethanolate. Preferred catalysts include Lewis acid metal compounds such as $AlX_3$, $TiX_3$, $TiX_4$, $VX_5$, $ZnX_2$, $FeX_3$ and $SnX_4$, wherein X is selected from the group consisting of hydrogen, acetoxy, alkoxy, arylalkoxy and aryloxy groups. Particularly preferred catalysts are homogeneous catalysts of formula $TiX_4$ wherein X may be the same or different and is selected from alkoxy groups containing from 1 to 6 carbon atoms, more preferably an ethoxy group or phenoxy group.

Suitably the concentration of catalyst is from 0.001 to 2 wt %, based on the total weight of the reactants containing the catalyst. Preferably the concentration is from 0.005 to 1 wt %, more preferably from 0.01 to 0.5 wt %.

In the second step the alkyl aryl carbonate undergoes disproportionation to yield diaryl carbonate and dialkyl carbonate. No additional catalyst is required for the disproportionation to take place.

The process takes place in apparatus comprising at least two distillation columns. The distillation columns are typical columns as used in chemical processes. Suitably the apparatus comprises at least three distillation columns. Preferably the apparatus comprises at least four distillation columns. Suitably the apparatus may be as described in WO2011067263. In a preferred embodiment of the invention the apparatus comprises at least two and preferably three reactive distillation columns. A "reactive distillation column" is a distillation column that contains a catalyst for effecting a chemical reaction in the distillation column. The reactive distillation columns are preferably followed by a further distillation column or columns that do not contain effective quantities of catalyst and that function as separation columns, separating the product, transesterification catalyst and byproducts.

The pressures in the at least two distillation columns may vary within wide limits. At least one of the distillation columns is operated at subatmospheric pressure which is achieved using vacuum equipment. In a preferred embodiment wherein three reactive distillation columns are used, the pressure at the top of the first distillation column may be 2 to 7 bar, preferably 2.5 to 5 bar. The pressure at the top of the second distillation column may be 0.1 to 3 bar, preferably 0.3 to 1.5 bar. The pressure at the top of the third distillation column may be 10 to 600 mbar, preferably 20 to 500 mbar. Preferably, the pressure at the top of the first distillation column is higher than that of the second distillation column which in turn is higher than that of the third distillation column. In another preferred embodiment wherein two reactive distillation columns are used the pressure at the top of the first distillation column may be 1.1 to 7 bar, preferably 2 to 5 bar. The pressure at the top of the second distillation column may be 0.01 to 1 bar, preferably 0.01 to 0.6 bar.

The temperatures in the one or more distillation columns may also vary within wide limits. The temperature at the bottom of the one or more distillation columns may be 50 to 350° C., preferably 120 to 280° C., more preferably 150 to 250° C., most preferably 160 to 240° C.

In addition to the distillation columns the apparatus comprises suitable piping and connections to appropriately link the distillation columns. The apparatus comprises vacuum equipment to create the subatmospheric pressure in at least one distillation column. Suitable vacuum equipment is well-known to the skilled person. The apparatus suitably also comprises suitable heating and cooling equipment to achieve the preferred temperatures in the distillation columns.

The apparatus suitably comprises at least one recycle loop whereby a reaction stream may be returned from one distillation column to an upstream distillation column. Preferably there is a recycle loop that enables the transesterification catalyst to be recycled from downstream reactive distillation columns to a reactive distillation column that is further upstream.

The at least one distillation column that is operated at subatmospheric pressure has undergone a leak test. A suitable leak test has the following steps:
(a) evacuate the distillation column to a vacuum under 500 mbar (e.g. 60 mbar)
(b) isolate the vacuum pump from the vessel and completely seal off the vessel
(c) measure the pressure increase in the vessel and determine the corresponding time The pressure increase in mbar divided by the time in minutes gives the vacuum loss in mbar/minute. With this value and the volume of the distillation column the air leakage rate in kg/h can be calculated using the following formula:

$$M_A = 0.071 \times \frac{\Delta p}{t} \cdot V$$

where $M_A$ is the air leakage in kg/h, $\Delta p$ is the change of pressure in mbar, t is the corresponding time in minutes and V is the plant volume in m³. The air leakage rate can be converted into an air leakage rate in mbar·L/s using the following conversion:

1 mbar·L/s=0.0043 kg/h Air of 20° C.

The leak test shows an air leakage rate of no greater than $2 \times 10^3$ mbar·L/s. Preferably the leak test shows an air leakage rate of no greater than $2 \times 10^4$ mbar·L/s. More preferably the leak test shows an air leakage rate of no greater than $2 \times 10^{-5}$ mbar·L/s. Most preferably the leak test shows an air leakage rate of no greater than $1.2 \times 10^{-5}$ mbar·L/s. It is desirable to have the lowest air leakage rate possible as this will reduce the problems of side reactions and catalyst deactivation. However, practical considerations will mean that there is a balance between minimising the air leakage rate and having an economic and effective apparatus.

In apparatus with multiple distillation columns that are operated at subatmospheric pressure, it is desirable that all these distillation columns have undergone a leak test and all show an air leakage rate of no greater than $2 \times 10^{-3}$ mbar·L/s. It is possible that one or more columns (particularly those that are not reactive distillation columns) could have a higher air leakage rate, but this is not preferred.

By following standard procedures for design and implementation of a process for preparing a diaryl carbonate, the skilled person would not have achieved an air leakage rate of no greater than $2 \times 10^3$ mbar·L/s. For example, the following guidance is given on the website of Thermo Systems Inc: for typical chemical process vacuum systems the design air leak rate (as a general rule based on experience with many successful applications), will be equal to the following amounts based on volume under vacuum in the 1 to 50 mm HgA range:

| Volume Under Vacuum (ft³) | Air Leak Rate (lb/hr) |
| --- | --- |
| 100 | 5 |
| 500 | 10 |
| 700 | 15 |
| 1000 | 20 |
| 1500 | 25 |
| 3000 | 50 |

This can be converted into m³ and an air leakage rate in mbar·L/s as follows:

| Volume Under Vacuum (m³) | Air Leakage Rate (mbar · L/s) |
| --- | --- |
| 2.8 | $9.8 \times 10^{-3}$ |
| 14 | $2.0 \times 10^{-2}$ |
| 20 | $2.9 \times 10^{-2}$ |
| 28 | $3.9 \times 10^{-2}$ |
| 42 | $4.9 \times 10^{-2}$ |
| 85 | $9.8 \times 10^{-2}$ |

As can be seen from the table, the air leakage rate obtained by following these guidelines is greater than the air leakage rate allowed in process of present invention.

The inventors have found that by minimising oxygen ingress into the apparatus, and specifically into the distillation column(s) operated at subatmospheric pressure, it is possible to reduce the problems of side reactions and catalyst deactivation. The skilled person must adopt a variety of measures to ensure that the leak test shows an air leakage rate of no greater than $2 \times 10^3$ mbar·L/s. One measure is to use equipment and procedures that are typically used in high vacuum systems. For example, the stems and flanges can all be tightened. Specially designed flanged connections, e.g. with groove and tongue or fine machined sealing surfaces and/or special seals, can be used. Instead of having flanged connections it may be desirable to have welded units wherein different pieces of apparatus are welded together, thus reducing the possibility of air ingress. Another measure is to use apparatus wherein purge gas (e.g. nitrogen) may be applied at the connection of the distillation columns with lines providing gas to and removing gas from the distillation columns. Such apparatus is disclosed in, for example, US2015136238. Flange elements may be connected to the lines and the one or more distillation columns and inner and outer gaskets may be positioned between the flanges. The purge gas may be applied between the inner and outer gaskets, helping to prevent air ingress at the connection between the line and the distillation column.

The present invention further provides a process for making a polycarbonate by preparing a diaryl carbonate according to the process of the present invention and reacting the diaryl carbonate with a dihydroxy aromatic compound. Preferably the dihydroxy aromatic compound is bisphenol A, which is 4,4'-(propan-2-ylidene)diphenol. Processes for preparing polycarbonates are disclosed in, for example, U.S. Pat. No. 5,747,609, WO2005026235 and WO2009010486.

The invention is further illustrated by means of the following experiment.

Thermal Degradation of Diphenyl Carbonate

An experiment was carried out to show that air ingress affects the thermal degradation of diphenyl carbonate. A series of 50 g samples of diphenyl carbonate of the same quality were heated in a 100 ml stainless steel closed vessel to the temperatures shown in table 1 for a period of 3 hours under nitrogen and under air, respectively. The APHA Pt—Co colour number, which is a yellowness scale defined by ASTM D1209, was measured for the DPC samples after heating:

TABLE 1

| Heating | APHA Pt—Co colour number | |
| --- | --- | --- |
| Temperature/Time | Under Nitrogen | Under Air |
| 90° C./3 hours | 6 | 6 |
| 140° C./3 hours | 6 | 7 |
| 160° C./3 hours | 6 | 9 |
| 180° C./3 hours | 6 | 13 |
| 220° C./3 hours | 7 | 18 |
| 255° C./3 hours | 10 | 28 |
| 280° C./3 hours | 19 | 52 |

A higher colour number (increased yellowness) is indicative of the degradation of diphenyl carbonate and the formation of colour bodies. This shows that air ingress (at an oxygen level of approximately 200 ppm in the above examples), particularly when accompanied by high temperatures, can cause degradation of diphenyl carbonate. If air leakage rates are not controlled and a process for preparing diphenyl carbonate is designed according to standard principles, then oxygen levels of 200 ppm could easily exist in the distillation columns, thus causing degradation of the product.

That which is claimed is:

1. A process for preparing a diaryl carbonate from a dialkyl carbonate and an aryl alcohol comprising:
   a first step wherein the dialkyl carbonate reacts with the aryl alcohol in the presence of a transesterification catalyst to provide alkyl aryl carbonate and alkyl alcohol; and
   a second step wherein the alkyl aryl carbonate undergoes disproportionation to yield diaryl carbonate and dialkyl carbonate;
   wherein the process takes place in apparatus comprising at least two distillation columns, and at least one of the distillation columns is operated at subatmospheric pressure which is achieved using vacuum equipment;
   and wherein the at least one distillation column that is operated at subatmospheric pressure has undergone a leak test and the leak test shows an air leakage rate of no greater than $2\times10^{-3}$ mbar·L/s.

2. The process according to claim 1, wherein the dialkyl carbonate is dimethyl carbonate or diethyl carbonate.

3. The process according to claim 1, wherein the aryl alcohol is phenol and the diaryl carbonate is diphenyl carbonate.

4. The process according to claim 1, wherein the transesterification catalyst is a homogeneous catalyst of formula $TiX_4$ wherein X may be the same or different and is selected from alkoxy groups containing from 1 to 6 carbon atoms.

5. The process according to claim 1, wherein the apparatus comprises at least two reactive distillation columns.

6. The process according to claim 5, wherein the apparatus comprises three reactive distillation columns.

7. The process according to claim 6, wherein the pressure at the top of a first reactive distillation column is from 2 to 7 bar, the pressure at the top of a second reactive distillation column is from 0.1 to 3 bar, and the pressure at the top of a third reactive distillation column is from 10 to 600 mbar, and the pressure at the top of the first reactive distillation column is higher than that of the second reactive distillation column which in turn is higher than that of the third reactive distillation column.

8. The process according to claim 1, wherein there is a connection between at least one distillation column operated at subatmospheric pressure and a line providing gas to or removing gas from the distillation column, and a purge gas is applied at the connection.

* * * * *